United States Patent [19]

Chasar

[11] Patent Number: 4,501,684

[45] Date of Patent: Feb. 26, 1985

[54] 2-NAPHTHYL PHOSPHORAMIDITES AND COMPOSITIONS THEREOF

[75] Inventor: Dwight W. Chasar, Northfield, Ohio

[73] Assignee: The B. F. Goodrich Company, Akron, Ohio

[21] Appl. No.: 505,540

[22] Filed: Jun. 17, 1983

[51] Int. Cl.³ .................................................. C09K 15/32
[52] U.S. Cl. .................................. 252/400 A; 260/959;
524/122; 544/157; 546/21
[58] Field of Search ............... 252/400.21; 260/239 A,
260/239 B, 959; 524/83, 96, 101, 122; 544/57,
157, 337; 546/21; 548/412

[56] References Cited

U.S. PATENT DOCUMENTS

| | | | |
|---|---|---|---|
| 3,531,483 | 9/1970 | Gilles | 544/221 |
| 3,673,181 | 6/1972 | Gutman | 544/157 |
| 3,702,837 | 11/1972 | Gilles | 524/101 |
| 3,909,491 | 9/1975 | Gilles | 252/400.21 |
| 4,062,909 | 12/1977 | Morgan et al. | 544/157 |
| 4,086,302 | 4/1978 | Morgan et al. | 544/157 |
| 4,418,022 | 11/1983 | Battey et al. | 252/400.21 |

*Primary Examiner*—Paul Lieberman
*Assistant Examiner*—Willie Thompson
*Attorney, Agent, or Firm*—J. Hughes Powell, Jr.; Alan A. Csontos

[57] ABSTRACT

2-naphthyl phosphoramidites are readily and inexpensively prepared by the reaction of N-dichlorophosphinoamines with a 2-naphthol in an alkylamine. The 2-naphthyl phosphoramidites are stabilizers for polymers such as the polyolefins and enhance the stabilizing activity of hydroxyphenylalkyleneyl isocyanurates.

14 Claims, No Drawings

2-NAPHTHYL PHOSPHORAMIDITES AND COMPOSITIONS THEREOF

BACKGROUND OF THE INVENTION

There have been a great variety of organic phosphites proposed for use as stabilizers for polymers, including the polyolefins. While some of these organic phosphites are available commercially, very few of them are completely satisfactory; and they are all expensive. Less expensive phosphorous containing chemicals that are readily prepared by incomplex methods and that have utility as stabilizers for polymers, particularly for polyolefins such as polypropylene, are needed. A further advantage would be that such phosphorous containing materials would enhance the stabilizing activity of hydroxyphenylalkyleneyl isocyanurates.

SUMMARY OF THE INVENTION

2-Naphthyl phosphoramidites are readily and inexpensively prepared by the reaction of N-dichlorophosphinoamines with a 2-naphthol in an alkylamine. The 2-naphthyl phosphoramidites are stabilizers for polymers such as the polyolefins and enhance the stabilizing activity of hydroxyphenylalkyleneyl isocyanurates.

DETAILED DESCRIPTION

The 2-naphthyl phosphoramidites may be represented by the general formula

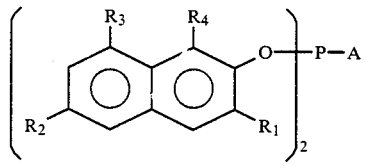

wherein A is:
(1)

wherein R is an alkyl radical containing 1 to 4 carbon atoms,
(2)

wherein a is 3 to 6, or
(3)

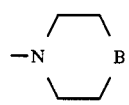

where B is —O—, —S—, or —NR; and $R_1$ and $R_2$ are hydrogen or alkyl, $R_3$ is hydrogen or t-butyl, and $R_4$ is hydrogen, or methyl, ethyl, propyl or isopropyl when $R_3$ is hydrogen, and at least one of $R_1$, $R_2$, $R_3$ and $R_4$ is an alkyl radical containing 1 to 4 carbon atoms. Preferably, $R_1$ and $R_2$ are isopropyl or t-butyl and $R_3$ and $R_4$ are hydrogen.

Preferably : in (1) R contains 4 carbon atoms; in (2) a is 4 to 5; in (3), B is —O—; $R_1$ and $R_2$ are isopropyl or t-butyl, and $R_3$ and $R_4$ are hydrogen.

Representative 2-naphthyl phosphoramidites include N,N-pentamethylene bis(3,6-di-t-butyl-2-naphthyl)-phosphoramidite, N,N-pentamethylene bis(3,6,8-tri-t-butyl-2-naphthyl)phosphoramidite, N,N-di-n-butyl bis(3,6-di-t-butyl-2-naphthyl)phosphoramidite, N,N-di-n-butyl bis(3,6,8-tri-t-butyl-2-naphthyl)phosphoramidite, N,N-oxydiethylene bis(3,6-di-t-butyl-2-naphthyl)-phosphoramidite, N,N-oxydiethylene bis(3,6,8-tri-t-butyl-2-naphthyl)phosphoramidite, and the like.

The 2-naphthyl phosphoramidites are prepared by the reaction of N-dichlorophosphinoamines with a 2-naphthol in the presence of an alkyl amine.

The N-dichlorophosphinoamines have the formula A—P—$CL_2$ wherein A is

wherein R is an alkyl radical containing 1 to 4 carbon atoms,

wherein a is 3 to 6 or

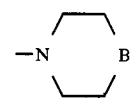

wherein B is —O—, —S—, or NR.

Representative N-dichlorophosphinoamines are N-dichlorophosphino-dimethylamine, N-dichlorophosphinodiethylamine, N-dichlorophosphino-dipropylamine, N-dichlorophosphino-diisopropylamine, N-dichlorophosphino-di-n-butylamine, N-dichlorophosphino-di-isobutylamine, N-dichlorophosphino-di-t-butylamine, N-dichlorophosphino-azetidine, N-dichlorophosphino-pyrrolidine, N-dichlorophosphino-piperidine, N-dichlorophosphino-morpholine, N-dichlorophosphino-thiomorpholine, and the like.

The substituted-2-naphthols may be represented by the general formula

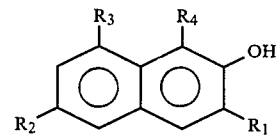

wherein at least one of $R_1$, $R_2$, $R_3$ and $R_4$ is an alkyl radical containing 1 to 4 carbon atoms, $R_1$ and $R_2$ are hydrogen or alkyl, $R_3$ is hydrogen or t-butyl, and $R_4$ is hydrogen, or may be methyl, ethyl, propyl or isopropyl when $R_3$ is hydrogen. Preferably, $R_1$ and $R_2$ are isopropyl or t-butyl and $R_3$ and $R_4$ are hydrogen. Typical substituted-2-naphthols are 3,6-di-t-butyl-2-naphthol, 3,6,8-tri-t-butyl-2naphthols, 3,6-di-t-butyl-8-methyl-2- naphtol, 1-methyl-3,6-di-t-butyl-2-naphthol, 3-t-butyl-2-naphthol, 6-t-butyl-2-naphthol, 1-methyl-6-t-butyl-2-naphthol, and the like.

In the representatives Examples I through VI, the 2-naphthol phosphoramidites were prepared by mixing one equivalent of a N-dichlorophosphinomine and two equivalents of a substituted 2-naphthol in triethylamine and refluxing the mixture for about 10 to 20 hours. The resulting product was cooled and filtered. The filtrate was evaporated to dryness and the dried product was washed with acetone or methanol and dried. The structures were confirmed by infrared spectroscopy and the molecular weights were determined by field desorption/mass spectrometry.

EXAMPLE I

N,N-pentamethylene bis(3,6-di-t-butyl-2-naphthyl)phosphoramidite 3.63 grams (0.0195 mol) of N-dichlorophosphino-piperidine and 10.0 grams (0.039 mol) of 3,6-di-t-butyl-2-naphthol were added to 50 ml of triethylamine and the mixture was refluxed for 20 hours. The reaction mixture was filtered and the filtrate was evaporated to dryness. This material was a yellow glass, and had a molecular weight of 625.

EXAMPLE II

N,N-pentamethylene bis(3,6,8-tri-t-butyl-2-naphthyl)phosphoramidite 2.98 grams (0.016 mol) of N-dichlorophosphino-piperidine and 10.0 grams (0.032 mol) of 3,6,8-tri-t-butyl-2-naphthol were added to 50 ml of triethylamine and the mixture was refluxed for 20 hours. The reaction mixture was filtered and the filtrate was evaporated to dryness. The dry product was washed with acetone and dried. 7 grams of the phosphoramidite was obtained. This material was an off-white powder, and had a melting point of 226°–240° C. The molecular weight was 737.

EXAMPLE III

N,N-di-n-butyl bis(3,6-di-t-butyl-2-naphthyl)phosphoramidite 4.49 grams (0.0195 mol) of N-dichlorophosphino-di-n-butylamine and 10.0 grams (0.039 mol) of 3,6-di-t-butyl-2-naphthol were added to 50 ml of triethylamine and the mixture was refluxed for 20 hours. The reaction mixture was filtered and the filtrate was evaporated to dryness. This material was a soft glass, and had a molecular weight of 669.

EXAMPLE IV

N,N-di-n-butyl bis(3,6,8-tri-t-butyl-2-naphthyl)phosphoramidite 3.68 grams (0.016 mol) of N-dichlorophosphino-di-n-butylamine and 10.0 grams (0.032 mol) of 3,6,8-tri-t-butyl-2-naphthol were added to 50 ml of triethylamine and the mixture was refluxed for 15 hours. The reaction mixture was filtered and the filtrate was evaporated to dryness. The dry product was washed with methanol and dried. 6.85 grams of the phosphoramidite was obtained. This material was an off-white powder, and had a melting point of 80°–125° C. The molecular weight was 781.

EXAMPLE V

N,N-oxydiethylene bis(3,6-di-t-butyl-2-naphthyl)phosphoramidite 1.83 grams (0.01 mol) of N-dichlorophosphino morpholine and 5.0 grams (0.02 mol) of 3,6-d-t-butyl-2-naphthol were added to 50 ml of triethylamine and the mixture was refluxed for 17 hours. The reaction mixture was filtered and the filtrate was evaporated to dryness. The dry product was washed with methanol and dried. 4.2 grams of the phosphoramidite was obtained. This material was a white powder, and had a melting point of 163°–167° C. The molecular weight was 627.

EXAMPLE VI

N,N-oxydiethylene bis(3,6,8-tri-t-butyl-2-naphthyl)phosphoramidite 1.51 grams (0.08 mol) of N-dichlorophosphino morpholine and 5.0 grams (0.016 mol) of 3,6,8-tri-t-butyl-2-naphthol were added to 50 ml of triethylamine and the mixture was refluxed for 19 hours. The reaction mixture was filtered and the filtrate was evaporated to dryness. The dry product was washed with methanol and dried. 4.0 grams of 2-naphthyl phosphoramidite was obtained. This material was a white powder and had a melting point of 230°–237° C. The molecular weight was 739.

Test samples of the substituted 2-naphthyl phosphoramidites in polypropylene were prepared by mixing the stabilizer compounds with polypropylene in a Brabender Plasticorder fitted with a Cam-Head (mixing chamber). The polypropylene is first masticated for 1½ minutes at 190° C. Then the stabilizer is added, followed by 3 minutes additional mixing. The mass is removed and pressed into 20 mil thick sheets. From these sheets are cut 1"×1" plaques for oven aging.

Thermal/oxidative stability (oven aging) testing consisted of aging the samples in triplicate in an air-circulating oven at 125° C. The time to catastrophic crumbling (failure) of the plaque was measured and reported as days to failure.

Each sample contained 0.1 weight part of phosphoramidite per 100 weight parts of polypropylene. The following results were obtained:

| | |
|---|---|
| N,N—pentamethylene bis(3,6-di-t-butyl-2-naphthyl) phosphoramidite | 5½ days. |
| N,N—pentamethylene bis(3,6,8-tri-t-butyl-2-naphthyl) phosphoramidite | 4 days. |
| N,N—di-n-butyl bis(3, 6-di-t-butyl-2-naphthyl) phosphoramidite | 4 days. |
| N,N—di-n-butyl bis(3,6,8-tri-t-butyl-2-naphthyl) phosphoramidite | 4 days. |

The hydroxyphenylalkyleneyl isocyanurate compounds useful in combination with the phosphoramidites of this invention have the formula

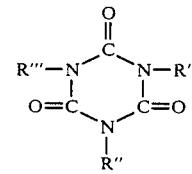

wherein R' is a hydroxyphenylalkyleneyl radical of the formula

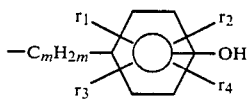

where m is 1 to 4, $r_1$ L is an alkyl radical having 1 to 18 carbon atoms and is positioned immediately adjacent to the hydroxy group on the ring; $r_2$, $r_3$, $r_4$ are hydrogen or an alkyl radical containing 1 to 18 carbon atoms; and $R''$ and $R'''$ are hydrogen, an alkyl radical containing 1 to 18 carbon atoms, or are the same as $R'$. A more preferred compound is when $R''$ and $R'''$ are equal to $R'$, i.e., all the R groups are hydroxyphenylalkyleneyl radicals, and $r_1$ is a t-alkyl radical containing from 4 to about 12 carbon atoms, $r_2$ is an alkyl radical containing from 1 to about 12 carbon atoms, $r_3$ and $r_4$ are hydrogen, and m is 1.

Even more preferred are the symmetrical tris (3,5-di-tert-alkyl-4-hydroxybenzyl) isocyanurates of the formula

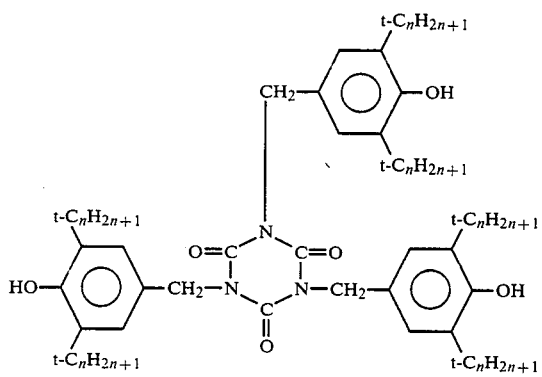

wherein n is 4 to 8.

Examples of the 4-hydroxybenzyl isocyanurate compounds are: tris(3-t-butyl-4-hydroxybenzyl) isocyanurate, tris(3-cetyl-4-hydroxybenzyl) isocyanurate, tris(3,5-dimethyl-4-hydroxybenzyl) isocyanurate, tris(3-methyl-5-isopropyl-4-hydroxybenzyl) isocyanurate, tris-(3,5-di-t-butyl-4-hydroxybenzyl) isocyanurate, tris(3-t-butyl-5-t-amyl-4-hydroxybenzyl) isocyanurate, tris[3,5-di(1-methyl-1-ethylpropyl)-4-hydroxybenzyl] isocyanurate, tris[3,5-di-(1,1,2,2-tetramethylpropyl)-4-hydroxybenzyl] isocyanurate, bis(3,5-dimethyl-4-hydroxybenzyl) isocyanurate, (3-methyl-4-hydroxybenzyl) isocyanurate, (3-t-butyl-4-hydroxybenzyl) isocyanurate and the like. Reference is made to U.S. Pat. No. 3,531,483 which discloses the isocyanurate compounds encompassed by this invention. This disclosure of this patent is incorporated herein by reference.

The amount of phosphoramidites used may vary from about 0.01 to 10 weight parts per 100 weight parts of material to be stabilized. More usually about 0.1 to 5.0 parts are used for mixtures with the hydroxyphenylalkyleneyl isocyanurate. The hydroxyphenylalkyleneyl isocyanurate compound is used at a level from about 0.01 part to about 1 to 5 parts by weight, and more preferably at from about 0.05 part to about 3 parts by weight per 100 parts by weight of the organic material. The phosphoramidite compound is employed at similar levels, i.e., from about 0.01 part to 5 parts and preferably at about 0.05 part to about 3 parts by weight per 100 parts by weight of organic material.

Thus the combined weight of the compounds is normally from about 0.02 part to about 10 parts and more preferably from about 0.05 to 5 parts by weight per 100 parts by weight of organic material. The hydroxyphenylalkyleneyl isocyanurate can be used in from about 10:1 to 1:10 weight ratio of isocyanurate compound to the phosphoramidite compound. Excellent results are obtained at about a 3:1 to 1:3 weight ratio. A 1:1 weight ratio of the compounds provides effective stabilization of organic materials.

To demonstrate the unexpected synergistic enhancement of antioxidant activity when the phosphoramites of this invention are combined with a hydroxyphenylalkyleneyl isocyanurate, test samples of polypropylene with 0.05 weight part each of tris(3,5-di-t-butyl-4-hydroxybenzyl)isocyanurate and the triaryl phosphites listed below were prepared and tested in the air oven until failure. The results obtained were as follows:

| | |
|---|---|
| N,N—pentamethylene bis(3,6-di-t-butyl-2-naphthyl) phosphoramidite | 33¼ days. |
| N,N—pentamethylene bis(3,6,8-tri-t-butyl-2-naphthyl) phosphoramitide | 19⅝ days. |
| N,N—di-n-butyl bis(3, 6-di-t-butyl-2-naphthyl) phosphoramidite | 29 days. |
| N,N—di-n-butyl bis(3,6,8-tri-t-butyl-2-naphthyl) phosphoramidite | 27¼ days. |

The combination of isocyanurate compound and the defined phosphoramidite compounds as defined herein provide exceptional heat stability to polyolefin polymers. The combination is especially useful for the stabilization of α-monoolefin homopolymers and copolymers, wherein the α-monoolefin contains 2 to about 8 carbon atoms. High and low-density polyethylene, isotactic and atactic polypropylene, poly-isobutylene, and poly(4-methyl-1-pentene) have excellent resistance to heat and oxygen when stabilized with the combinations of the present invention. Ethylene-propylene copolymers and ethylene-propylene terpolymers, generally containing less than about 10 percent by weight of one or more monomers containing multiple unsaturation provided, for example, by 1,4-hexadiene, dimethyl-1,4,9-decatriene, dicyclopentadiene, vinyl norborene, ethylidene norborene, and the like, also provide excellent ageing properties using the composition of this invention.

Other organic materials which can be stabilized in accordance with the present invention include both natural and synthetic polymers. For example, the stabilizers are useful for the stabilization of cellulosic materials; natural rubber, halogenated rubber, conjugated diene polymers, as, for instance, polybutadiene, copolymers of butadiene with styrene, acrylonitrile, acrylic acid, alkyl acrylates or methacrylates, methyl vinyl ketone, vinyl pyridine, etc.; polyisoprene, polychloroprene, and the like; vinyl polymers such as poly(vinyl chloride), poly(vinylidene chloride), copolymers of vinyl chloride with vinylidene chloride, polyvinyl acetate, copolymers or vinyl halide with butadiene, styrene, vinyl esters, α,β-unsaturated ketones and aldehydes, and the like; homopolymers and copolymers of acrylic monomers such as acrylic acid, methacrylic acid, methyl acrylate, methyl methacrylate, ethyl acrylate, 3-ethylhexyl acrylate, acrylamide, methacrylamide, N-methylol-acrylamide, haloacrylates, acrylonitrile, methacrylonitrile, haloacrylates, and the like; epihalohydrin polymers; polyether- or polyolderived polyurethanes; acetal homopolymers and copolymers; polycarbonates; polyesters such as those derived from maleic, fumaric, itaconic, or terephthalic anhydrides; for example, polyethylene terephthalate; polyamides such as those derived from the reaction of hexamethylenediamine with adipic or sebacic acid; epoxy resins such as those obtained from the condensation of epichlorohydrin with bisphenols; ring opened olefin polymers and the like. Polymer blends, that is, physical admixture of two or more polymers may also be stabilized in accordance with the present invention.

In addition to polymeric materials, the present compounds may stabilize a wide variety of other organic materials. Such compounds include: waxes, synthetic and petroleum-derived lubricating oils and greases; animal oils such as, for example, fat, tallow, lard, cod-liver oil, sperm oil; vegetable oils such as castor, linseed, peanut, palm, cotton seed, and the like; fuel oil; diesel oil, gasoline and the like.

The compounds are readily incorporated into materials to be patented by dissolving or dispersing them with the materials, in liquids, dispersions, solutions, and solid forms. If the material is a solid, especially a polymeric solid such as rubber or a plastic, the compounds can be admixed using mixers such as Banburys, extruders, two-roll mills, and the like, following conventional techniques. One way to disperse the compounds in plastic materials is to dissolve or suspend the compounds in a solvent or diluent, mix the mixture with a plastic in powder or solution form, and then evaporate the solvent.

Compositions containing the novel compounds and combination of compounds can also contain other known compounding ingredients such as fillers like carbon black, silica, metal carbonates, talc, and the like; pigments and colorants; curative ingredients like sulfur and peroxides, and vulcanization accelerators; fungicides; processing aids, reinforcing agents and standard ingredients known to the art. Other ingredients known in the art as ultra violet light, thermal and/or oxidative stabilizers can also be used in the stabilized compositions.

I claim:

1. 2-naphthyl phosphoramidites of the general formula

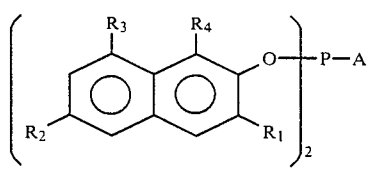

wherein A is

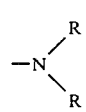

wherein R is an alkyl radical containing 1 to 4 carbon atoms;

wherein a is 3 to 6; or

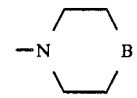

where B is —O—, —S—, or —NR; $R_1$ and $R_2$ are hydrogen or alkyl, $R_3$ is hydrogen or t-butyl, and $R_4$ is hydrogen or methyl, ethyl, propyl or isopropyl when $R_3$ is hydrogen, and at least one of $R_1$, $R_2$, $R_3$ and $R_4$ is an alkyl radical containing 1 to 4 carbon atoms.

2. 2-naphthyl phosphoramidites of claim 1 wherein in (1) R contains 4 carbon atoms; in (2) a is 4 to 5; in (3) B is —O—; $R_1$ and $R_2$ are isopropyl or t-butyl, and $R_3$ and $R_4$ are hydrogen.

3. Compositions of claim 2: N,N-pentamethylene bis(3,6-di-t-butyl-2-naphthyl)phosphoramidite, N,N-pentamethylene bis(3,6,8-tri-t-butyl-2-naphthyl)phosphoramidite, N,N-di-n-butyl bis(3,6-di-t-butyl-2-naphthyl)phosphoramidite, N,N-di-n-butyl bis(3,6-tri-t-butyl-2-naphthyl)phosphoramidite, N,N-oxydiethylene bis(3,6-di-t-butyl-2-naphthyl)phosphoramidite, and N,N-oxydiethylene bis(3,6,8-tri-t-butyl-2-naphthyl)phosphoramidite.

4. Compositions comprising organic materials subject to degradation and stabilizing amounts of 2-naphthyl phosphoramidites of the general formula

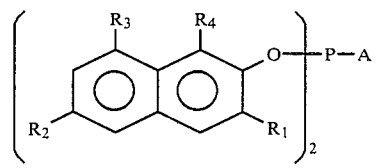

wherein A is

wherein R is an alkyl radical containing 1 to 4 carbon atoms;

wherein a is 3 to 6; or

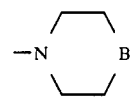

where B is —O—, —S—, or —NR; $R_1$ and $R_2$ are hydrogen or alkyl, $R_3$ is hydrogen or t-butyl, and $R_4$ is hydrogen or methyl, ethyl, propyl or isopropyl when $R_3$ is hydrogen, and at least one of $R_1$, $R_2$, $R_3$ and $R_4$ is an alkyl radical containing 1 to 4 carbon atoms.

5. Compositions of claim 4 wherein the organic material is a polymer and in (1) R contains 4 carbon atoms; in (2) a is 4 to 5; in (3) B is —O—; and $R_1$ and $R_2$ are isopropyl or t-butyl and $R_3$ and $R_4$ are hydrogen.

6. Compositions of claim 5 wherein 2-naphthyl phosphoramidite is N,N-pentamethylene bis(3,6-di-t-butyl-2-naphthyl)phosphoramidite, N,N-pentamethylene bis(3,6,8-tri-t-butyl-2-naphthyl)phosphoramidite, N,N-di-n-butyl bis(3,6-di-t-butyl-2-naphthyl)phosphoramidite, N,N-di-n-butyl bis(3,6,8-tri-t-butyl-2-naphthyl)phosphoramidite, N,N-oxydiethylene bis(3,6-di-t-butyl-2-naphthyl)phosphoramidite, and N,N-oxydiethylene bis(3,6,8-tri-t-butyl-2-naphthyl)phosphoramidite.

7. Stabilizer compositions comprising (1) 2-naphthyl phosphoramidites of the general formula

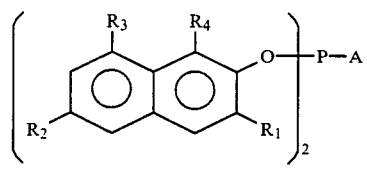

wherein A is

wherein R is an alkyl radical containing 1 to 4 carbon atoms;

wherein a is 3 to 6; or

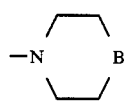

where B is —O—, —S—, or —NR; $R_1$ and $R_2$ are hydrogen or alkyl, $R_3$ is hydrogen or t-butyl, and $R_4$ is hydrogen or methyl, ethyl, propyl or isopropyl when $R_3$ is hydrogen, and at least one of $R_1$, $R_2$, $R_3$ and $R_4$ is an alkyl radical containing 1 to 4 carbon atoms; and (2) hydroxyphenylalkyleneyl isocyanurates of the formula

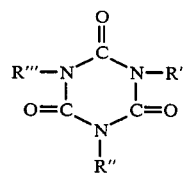

wherein R' is a hydroxyphenylalkyleneyl radical of the formula

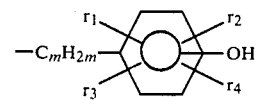

where m is 1 to 4, $r_1$ is an alkyl radical having 1 to 18 carbon atoms and is positioned immediately adjacent to the hydroxy group on the ring; $r_2$, $r_3$, and $r_4$ are hydrogen or an alkyl radical containing 1 to 18 carbon atoms; and R" and R''' are hydrogen, an alkyl radical containing 1 to 18 carbon atoms, or are the same as R'.

8. Compositions of claim 7 wherein in (1) R contains 4 carbon atoms; in (2) a is 4 to 5; in (3) B is —O—; $R_1$ and $R_2$ are isopropyl or t-butyl, $R_3$ and $R_4$ are hydrogen; and in (2) R" and R''' are equal to R', $r_1$ is a tertiary alkyl radical containing 4 to 12 carbon atoms, $r_2$ is an alkyl radical containing 1 to 12 carbon atoms, $r_3$ and $r_4$ are hydrogen, and m is 1.

9. A composition of claim 8 wherein (1) is N,N-pentamethylene bis(3,6-di-t-butyl-2-naphthyl)phosphoramidite, N,N-pentamethylene bis(3,6,8-tri-t-butyl-2-naphthyl)phosphoramidite, N,N-di-n-butyl bis(3,6-di-t-butyl-2-naphthyl)phosphoramidite, N,N-di-n-butyl bis(3,6,8-tri-t-butyl-2-naphthyl)phosphoramidite, N,N-oxydiethylene bis(3,6-di-t-butyl-2-naphthyl)phosphoramidite, or N,N-oxydiethylene bis(3,6,8-tri-t-butyl-2-naphthyl)phosphoramidite; and (2) has the formula

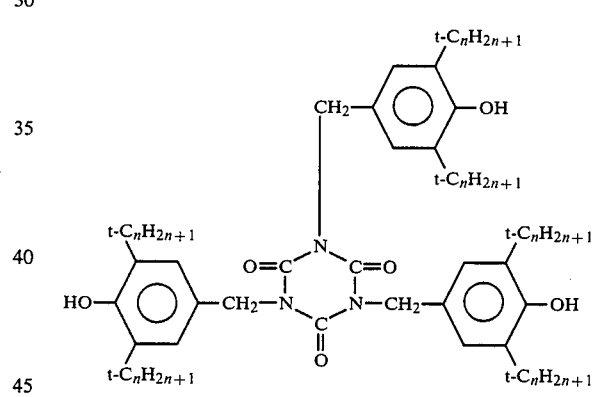

wherein n is 4 to 8.

10. A composition of claim 9 where (2) is 1,3,5-tris(3,5-di-t-butyl-4-hydroxybenzyl)isocyanurate.

11. Compositions comprising organic materials subject to degradation and stabilizing amounts of (1) 2-naphthyl phosphoramidites of the general formula

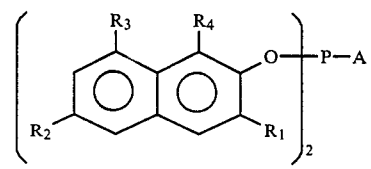

wherein A is

wherein R is an alkyl radical containing 1 to 4 carbon atoms;

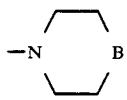

wherein a is 3 to 6; or

where B is —O—, —S—, or —NR; $R_1$ and $R_2$ are hydrogen or alkyl, $R_3$ is hydrogen or t-butyl, and $R_4$ is hydrogen or methyl, ethyl, propyl or isopropyl when $R_3$ is hydrogen, and at least one of $R_1$, $R_2$, $R_3$ and $R_4$ is an alkyl radical containing 1 to 4 carbon atoms; and (2) hydroxyphenylalkyleneyl isocyanurates of the formula

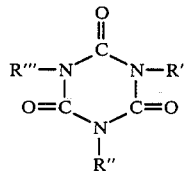

wherein R' is a hydroxyphenylalkyleneyl radical of the formula

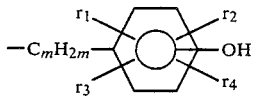

where m is 1 to 4, $r_1$ is an alkyl radical having 1 to 18 carbon atoms and is positioned immediately adjacent to the hydroxy group on the ring; $r_2$, $r_3$, and $r_4$ are hydrogen or an alkyl radical containing 1 to 18 carbon atoms; and R″ and R‴ are hydrogen, an alkyl radical containing 1 to 18 carbon atoms, or are the same as R′.

12. Compositions of claim 11 wherein in (1) R contains 4 carbon atoms; in (2) a is 4 to 5; in (3) B is —O—; $R_1$ and $R_2$ are isopropyl or t-butyl, and $R_3$ and $R_4$ are hydrogen, and in (2) R″ and R‴ are equal to R′, $r_1$ is a tertiary alkyl radical containing 4 to 12 carbon atoms, $r_2$ is an alkyl radical containing 1 to 12 carbon atoms, $r_3$ and $r_4$ are hydrogen, and m is 1.

13. A composition of claim 12 wherein (1) is N,N-pentamethylene bis(3,6-di-t-butyl-2-naphthyl)phosphoramidite, N,N-pentamethylene bis(3,6,8-tri-t-butyl-2-naphthyl)phosphoramidite, N,N-di-n-butyl-bis(3,6-di-t-butyl-2-naphthyl)phosphoramidite, N,N,-di-n-butyl bis(3,6,8-tri-t-butyl-2-naphthyl)phosphoramidite, N,N-oxydiethylene bis(3,6-di-t-butyl-2-naphthyl)phosphoramidite, or N,N-oxydiethylene bis(3,6,8-tri-t-butyl-2-naphthyl)phosphoramidite; and (2) has the formula

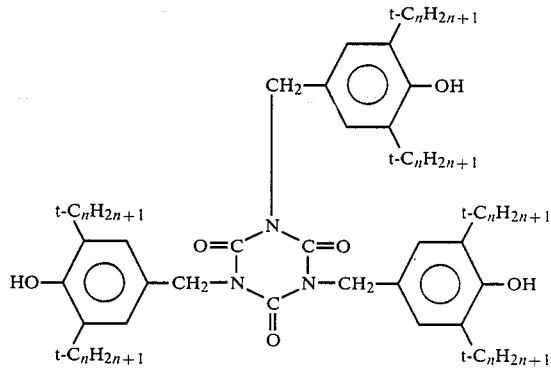

wherein n is 4 to 8.

14. A composition of claim 13 where (2) is 1,3,5-tris(3,5-di-t-butyl-4-hydroxybenzyl)isocyanurate.

* * * * *